United States Patent
Stalnaker et al.

(10) Patent No.: US 6,615,672 B2
(45) Date of Patent: Sep. 9, 2003

(54) APPARATUS AND METHOD FOR DETERMINING RESIDUAL SEAL FORCE OF SEALED CONTAINERS

(75) Inventors: Thomas A. Stalnaker, West Chester, PA (US); Bruce Smith, West Chester, PA (US)

(73) Assignee: Genesis Machinery Products, Exton, PA (US)

(*) Notice: Subject to any disclaimer, the term of this patent is extended or adjusted under 35 U.S.C. 154(b) by 0 days.

(21) Appl. No.: 09/949,297

(22) Filed: Sep. 7, 2001

(65) Prior Publication Data

US 2003/0047005 A1 Mar. 13, 2003

(51) Int. Cl.[7] ................................................. G01N 3/08
(52) U.S. Cl. ............................................. 73/818; 73/52
(58) Field of Search ..................... 73/52, 49.3, 818; 702/41, 42

(56) References Cited

U.S. PATENT DOCUMENTS

| | | | | |
|---|---|---|---|---|
| 4,511,044 A | * | 4/1985 | Connor et al. ............... 209/522 |
| 4,922,746 A | * | 5/1990 | Hulsman et al. ............. 73/49.3 |
| 5,285,678 A | * | 2/1994 | McDaniel et al. ........... 73/49.3 |

* cited by examiner

*Primary Examiner*—Edward Lefkowitz
*Assistant Examiner*—Corey D. Mack
(74) *Attorney, Agent, or Firm*—Eugene E. Renz, Jr.

(57) ABSTRACT

The invention is an apparatus and method for testing the residual seal force of the closure of a container, particularly a container for parenteral pharmaceutical products. An automated and instrumented press collects stress and strain data for a closure of a container for parenteral pharmaceutical products. An algorithm is automatically applied to the resulting data set, determining candidate residual seal forces for several data smoothing spans. Confidence levels are determined for each of the candidate residual seal forces. The candidate residual seal force corresponding to the highest confidence level is selected. The process is repeated and the results averaged to determine a final residual seal force.

31 Claims, 14 Drawing Sheets

Calculate first confidence factor based on comparing the minimum (valley) in the second derivative analogue to the second minimum value.

Calculate the second confidence factor based on comparing the depth of the second derivative analogue valley (minimum) to the width of the valley.

Calculate the third confidence factor based on the drop in the first derivative analogue from the peak to the valley. If no peak and valley, use 25.

Determine the hysteresis band for counting crossings as ¼ of the second derivative analogue minimum, above and below 0.

Count the number of crossings of the second derivative analogue through the hysteresis band from above to below and from below to above.

Repeat for each data smoothing span for which a valley was found in the second derivative analogue.

FIG. 11D

APPARATUS AND METHOD FOR DETERMINING RESIDUAL SEAL FORCE OF SEALED CONTAINERS

BACKGROUND OF THE INVENTION

1. Field of the Invention

The invention is an apparatus and method for determining the residual seal force of sealed containers. The invention particularly relates to the monitoring of production of parenteral pharmaceutical products, but can be applied to the determination of residual seal forces for many types of containers and for many types of products.

2. Description of the Related Art

Parenteral (injectable) pharmaceutical products are usually packaged in glass containers with a closure comprising a resilient sealing element held in place over the open end of the container by a cap. The cap usually is composed of aluminum, but may be composed of other materials. In the pharmaceutical packaging process, an apparatus applies a force to the resilient member, compressing the resilient member between a flange of the container and the cap. A skirt of the cap is crimped around the flange of the container. The cap thereby maintains a force on the resilient member, compressing the resilient member, sealing the container and protecting the pharmaceutical product against contamination.

The force exerted by the resilient member on the cap and container flange of a sealed container, and hence by the cap and container flange on the resilient member, is hereinafter referred to as the "residual seal force" ("RSF"). The compression of the resilient member in response to the residual seal force is hereinafter referred to as the "residual compression." Maintenance of an adequate residual seal force and hence a proper residual compression of the resilient member is important to maintaining a proper seal and to protecting the integrity of the pharmaceutical product enclosed within the container.

For purposes of this application, the term "closure" is an assembly comprising the flange of the container, the resilient member covering the opening of the container and the cap compressing the resilient member and thereby sealing the container. A "closure" may include a removable button allowing access to the resilient member so that a syringe may be inserted into the container, providing access to the parenteral pharmaceutical product.

Testing of the residual seal force of the closure is an important step in the package development and production of parenteral pharmaceutical products. The residual seal force of the closure may be tested in any of several ways. Selected containers may be tested by manually gripping the cap and attempting to rotate the cap. If the cap does not rotate, the closure is assumed to be adequately tight. The manual testing process is subjective, operator-dependent, imprecise and does not allow proactive process control.

Testing equipment exists, as described in U.S. Pat. Nos. 4,315,427 and 4,337,644 both issued to Leiter on Feb. 16, 1982 and Jul. 6, 1982 respectively. The Leiter patents reveal an apparatus and method whereby a slowly increasing force is applied to the closure while a human operator observes the skirt of the cap using a microscope. When the operator observes movement of the skirt, the operator assumes that the residual compression of the resilient member has been overcome and that the force exerted to overcome that residual compression equals the residual seal force. The Leiter apparatus and method is a manual method subject to operator control and operator error.

No existing method or apparatus provides for the automated testing of container closures for parenteral pharmaceutical products. No existing method or apparatus provides the algorithm of the present invention for determining residual seal force from stress-strain data collected by an automated testing apparatus.

SUMMARY OF THE INVENTION

The invention is an apparatus and method for determining the residual seal force for containers, particularly containers for parenteral pharmaceutical products. An automated press moves an anvil against the closure of a sealed container. The press automatically records distance as the anvil moves. At prescribed distances, the press automatically records the force applied to the anvil by the closure. The resulting data set comprises a sequence of data points for strain data (displacement of the closure) and stress data (force exerted by the closure in response to the strain). The data points can be plotted on a graph, approximating a stress-strain curve.

Stress-strain curves for the testing of parenteral container closures follow a predictable pattern. At the point at which the force exerted by the press overcomes the residual force exerted by the residual compression of the resilient member, the stress vs. strain graph shows a "knee" resulting from a reduction in slope. The stress at the knee of the stress-strain curve therefore defines the residual seal force.

The invention applies an algorithm to locate the knees of a series of data sets and hence to determine residual seal force. The strategy of the algorithm is to locate the knee using the technique of finding a minimum in the second derivative of the data set. In theory, location of a knee using a second derivative should be a straightforward exercise. In practice, the knee of the stress-strain curve is a subtle feature and difficult to isolate. The construction and configuration of containers coupled with limitations in the data collection create uncertainty and noise in the data and obscure the location of the knee. For example, the deformation of the button and cap are reflected in the stress-strain data, but do not represent the residual seal force. The algorithm of the present invention allows the knee, and hence the residual seal force, to be located despite the noise and uncertainty.

Since the data are discrete rather than a mathematical function, numerical analysis methods are used to determine a first derivative analogue and a second derivative analogue based on changes in slope over the span of two or more data points. Because the data are subject to minute variations due to the physics of the data collection and because derivatives tend to exacerbate these variations, data smoothing is used to reduce the variations. The first derivative analogue is determined and used to identify a strain range of interest. The strain range of interest comprises the region of the stress-strain curve falling between a lower bound defined by a local maximum of the first derivative analogue and an upper bound defined by a subsequent local minimum of the first derivative analogue. The minimum value of the second derivative analogue falling within the range of interest identifies a first possible location of the "knee" and hence a first candidate residual seal force.

The calculations are repeated using different data smoothing criteria. Several different data smoothing criteria are applied and a "candidate residual seal force" is calculated for each data-smoothing criterion. A "confidence level" is calculated for each candidate residual seal force. The confidence level represents an expression of the relative confidence that a particular candidate residual seal force is correct.

Four factors are used to calculate a confidence level. The first factor compares the value of the minimum of the second derivative analogue falling within the range of interest and the next-lowest minimum of the second derivative analogue occurring at any point in the data set. The greater the difference, the greater the confidence.

The second factor compares the value of the second derivative analogue minimum and the width of the second derivative analogue valley. The narrower and deeper the valley, the greater the confidence.

The third factor compares the first derivative analogue local maximum and the first derivative analogue valley used to define the range of interest. The greater the difference, the greater the confidence.

The fourth factor compares the value for residual seal force in question to the other values for residual seal force calculated using the same data points for other data smoothing criteria. The greater the agreement between the values, the greater the confidence.

The geometric mean of the four factors is calculated by multiplying the four factors and taking the fourth root of the resulting product. The geometric mean is adjusted to consider the variability in the data. The adjustment comprises drawing a hysteresis band on the graph of the second derivative analogue. The number of times that the graph of the second derivative analogue crosses through the hysteresis band is counted and the resulting number is subtracted from the geometric mean of the four factors. The result is the confidence level.

The candidate residual seal forces are ranked by confidence level. The calculated residual seal force corresponding to the data smoothing criterion producing the highest confidence level is selected as the residual seal force for the particular set of data points. The entire process is repeated twice, resulting in three sets of data points and three values for residual seal force.

If the three results agree adequately, the data is accepted and the three values are arithmetically averaged to determine the final residual seal force. If the three results do not agree, the result is rejected and additional data collected.

In the method of the invention, data collection is automated, as are data manipulation and calculation. The value for residual seal force determined for a container may be used to control a process, such as a packaging process for pharmaceutical or other products. The determined value of residual seal force for a container also may be used to design or select appropriate packaging for a product, such as a pharmaceutical product.

BRIEF DESCRIPTION OF THE DRAWINGS

FIGS. 11A through 11F is a detailed flow chart.

DESCRIPTION OF THE PREFERRED EMBODIMENT

Figure 1:
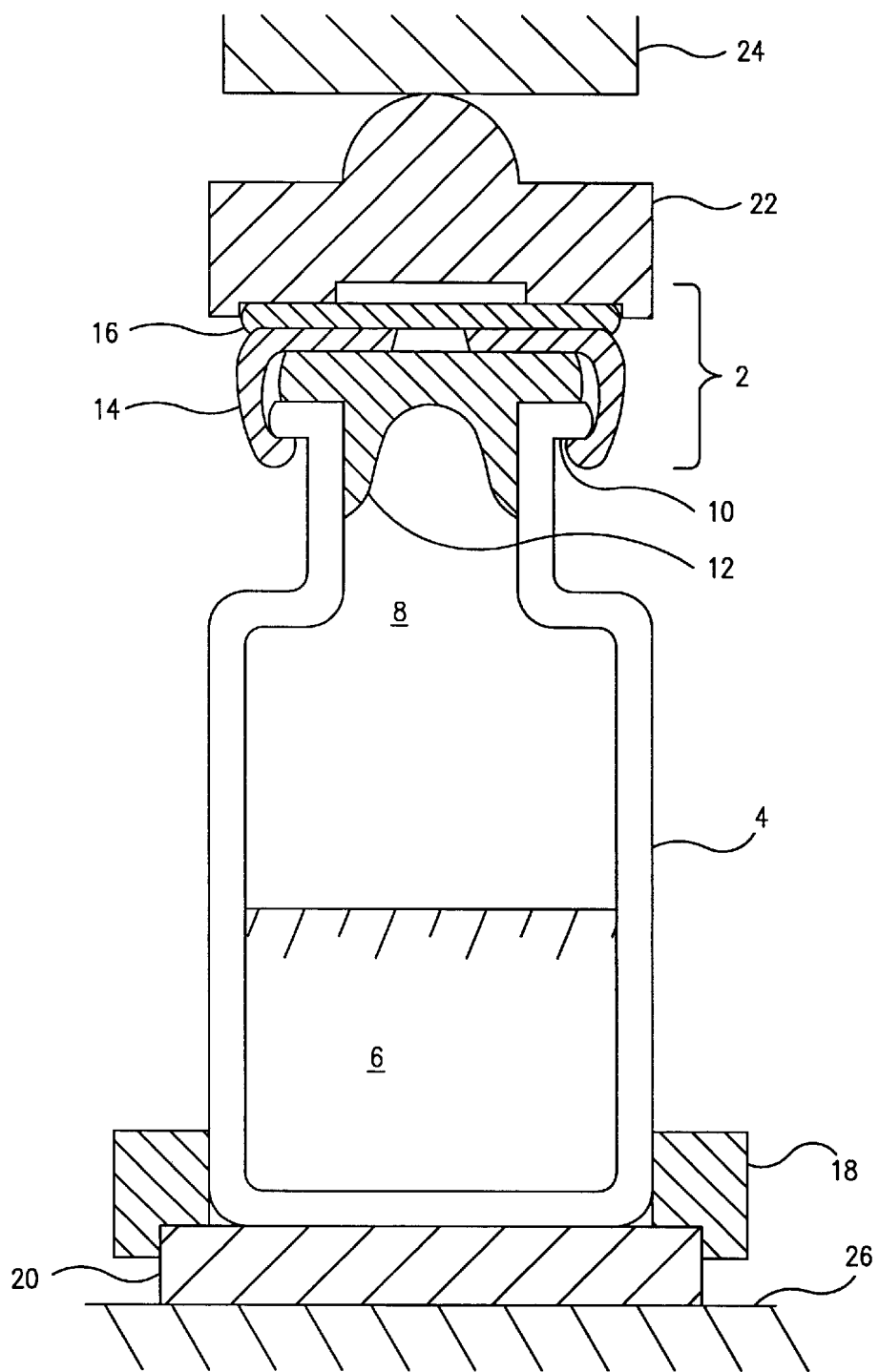
FIG. 1 is a sealed container undergoing testing.

The closure 2 of a container 4 for a parenteral pharmaceutical product 6 is illustrated by FIG. 1. The container 4 has an opening 8 and a flange 10. A resilient member 12 covers the opening 8. A cap 14 is crimped under flange 10 and compresses resilient member 12, sealing opening 8. An optional removable button 16 provides access to the resilient member 12 and allows the contents 6 of container 4 to be removed using a syringe. The residual compression of resilient member 12 maintained by cap 14 causes the residual seal force that seals container 4 and prevents contamination of the pharmaceutical product 6.

Figure 2:
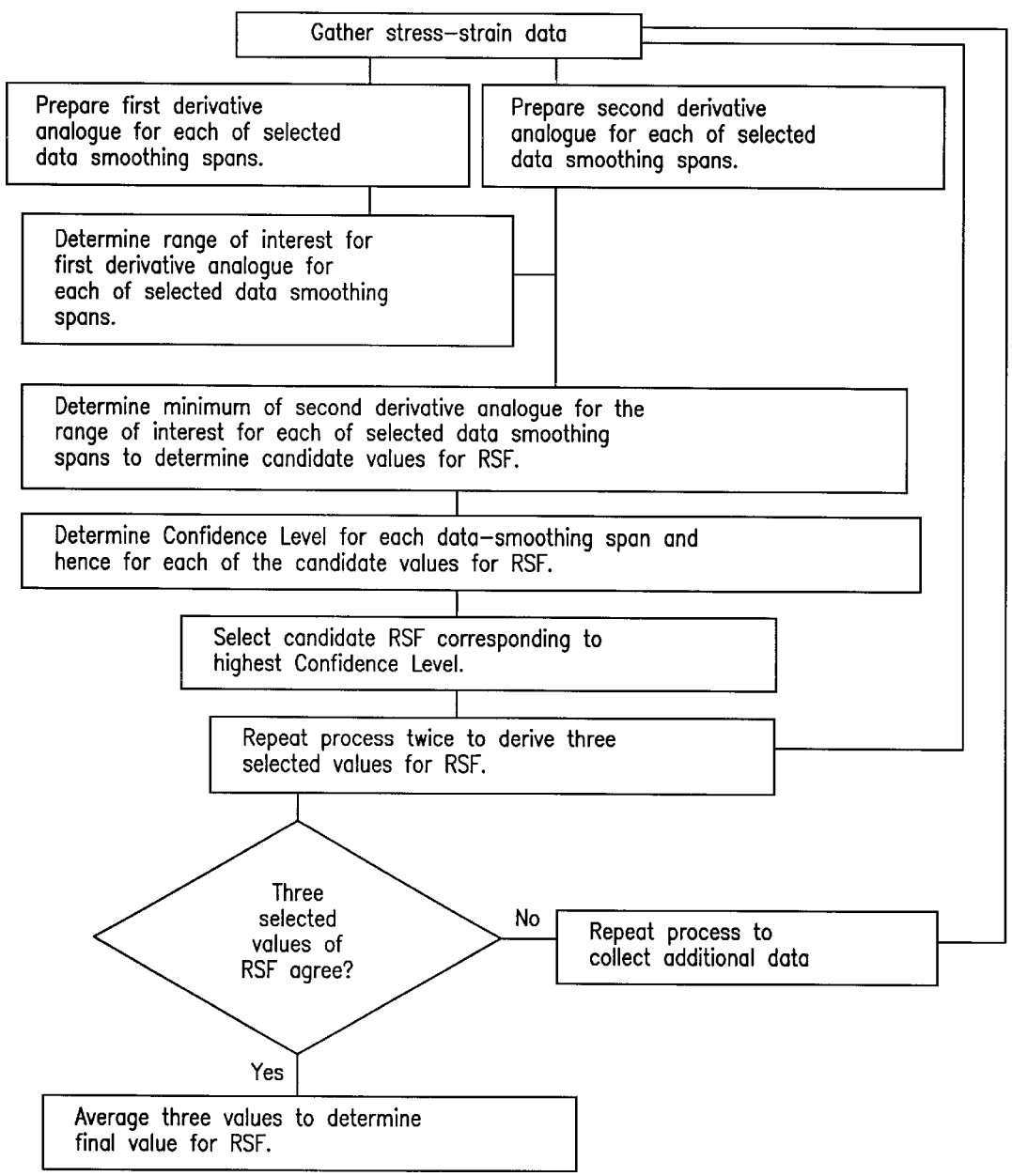
FIG. 2 is a flow chart of the method of the present invention.
Figure 3:
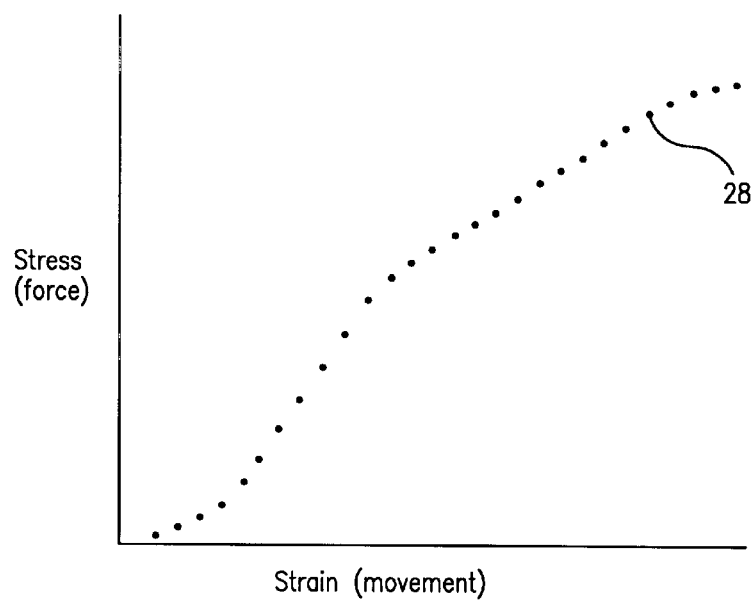
FIG. 3 is an example data set graph.

As shown by the flow chart of FIG. 2, the method of the invention allows automated testing the residual seal force of closure 2. The first step of the method of the invention is to gather stress-strain data concerning a container closure 2. To gather the data, a sealed container 4 is placed on an appropriate container holder 18 (FIG. 1) on a base 20 of an appropriate press 26. An anvil 22 is placed on the button 16. The force reading is zeroed and the push rod 24 of the press 26 is advanced in contact with the anvil 22. The push rod 24 and base 20 of the press 26 compress the resilient member 12 between the rigidly supported container 4 and the anvil 22. The preferred rate of advance of the anvil 22 is a constant 0.01 inches/second. For every 0.001 inches or less of travel, the press 26 automatically records as stress data the force exerted by the container closure 2 in response to the movement (strain) imposed upon the is container closure 2 by the anvil 22. The press 26 also automatically records the corresponding strain data. The resulting data set 28 comprises a sequence of stress-strain measurements that can be graphed, as illustrated by FIG. 3. The data set 28 approximates a curve of predictable shape.

From FIG. 2, the next step of the method is to prepare analogues of first and second derivative of the data set 28. Since the data set 28 comprises distinct data points rather than a function, numerical techniques are used to approximate the first and second derivatives. A plurality of smoothing spans are sequentially applied to the determination of first and second derivative analogues. The number of smoothing spans and the parameters of each span are selected based on experience for each application to provide a range of first and second derivative analogue curves of sufficient accuracy and to be compatible with data processing capabilities of the apparatus used to evaluate the data set.

Figure 4:
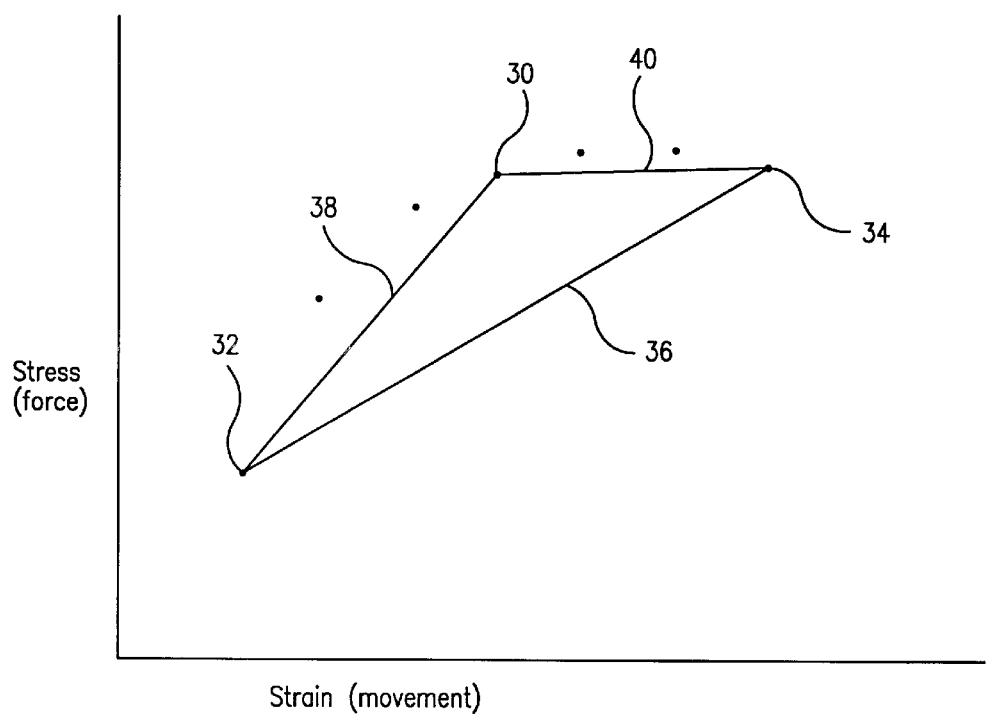
FIG. 4 is a detail of a data set graph illustrating calculation of the first and second derivative analogue.

FIG. 4 is a detail of the graphed stress-strain data set 28 illustrating calculation of the first and second derivative analogues for an example data smoothing span of three. To determine the first derivative analogue for a first data point 30, a second data point 32 appearing one smoothing span (in this case three data points behind data point 30 and a third data point 34 appearing one smoothing span (again three) data points ahead of the first data point 30 in the sequence are located. Second and third data points 32 and 34 define a first line segment 36. The slope of the first line segment 36 approximates the first derivative of a function describing data set 28 at first data point 30, and is referred to in this application as the "first derivative analogue" for first data point 30. The first derivative analogue is determined similarly for each data point in data set 28 and for each of the plurality of smoothing spans. First derivative analogues are calculated in units of lbf./inch.

Referring again to FIG. 4, to determine the second derivative analogue for first data point 30 for a data smoothing span of three, the data points appearing one smoothing span (three in the example) data points behind and one smoothing span (again three) data points ahead of data point 24 are again located. These data points are again second and third data points 32 and 34. First and second data points 30 and 32 define a second line segment 38 and first and third data points 30 and 34 define a third line segment 40. The difference between the slopes of the second line segment 38 and third line segment 40 approximates the second derivative of a function describing data set 28 at data point 30, and is referred to in this application as the "second derivative analogue" for first data point 30. The second derivative analogue is determined for each data point in data set 28 for each of the selected data smoothing spans. Second derivative analogues are calculated in units of lbf./inch/inch.

Figure 5:
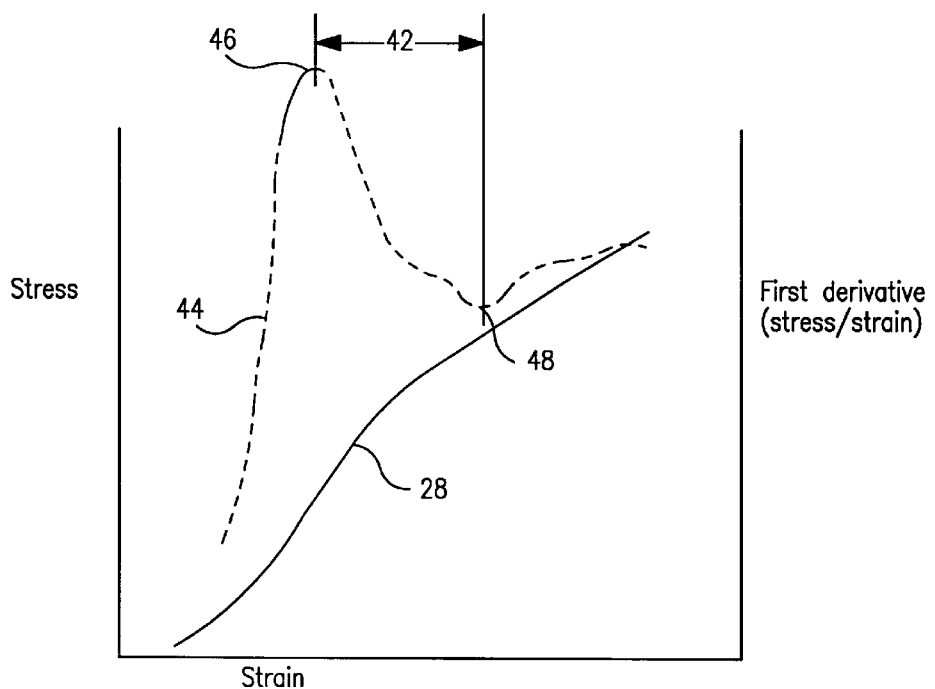
FIG. 5 is an example of a first derivative analogue.

From FIG. 2, the next step of the invention is to determine a range of interest 42. In FIG. 5, a solid curve represents the graph of data set 28 and a dashed line represents a graph of the first derivative analogue 44. The expected pattern of the first derivative analogue graph 44 is a rise to above half of the first derivative analogue's maximum value, followed by a peak, followed by a drop of at least 10% from the peak, followed by a valley, followed by a rise of at least is 10% (or reaching the end of the data).

Each of the first derivative analogue values for the data set 28 is examined sequentially to determine the first derivative local maximum value 46. The first derivative analogue local maximum 46 is the maximum value of the first derivative analogue that is followed by a drop in value of at least 10% from the maximum value. The examination of the first derivative analogues continues sequentially until a succeeding first derivative local minimum 48 is located. The examination ceases when the value of the first derivative analogue rises 10% above the first derivative analogue local minimum 48. The values for strain appearing between the first derivative local maximum 46 and the first derivative local minimum 48 define the range of interest 42. A range of interest 42 is determined for each selected data-smoothing span.

Figure 6:
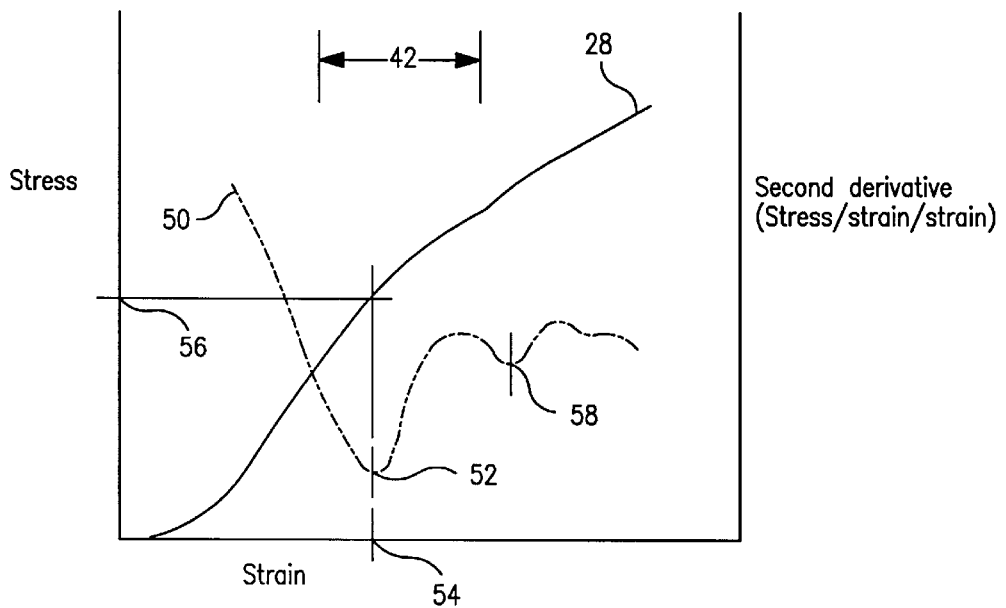
FIG. 6 is an example of a second derivative analogue.

FIG. 6 shows an example of the second derivative analogue graph 50 (dotted and dashed line) along with the stress-strain curve (solid line) approximating data set 28. The minimum 52 of the second derivative analogue 50 appearing in the range of interest 42 is located and the value of the strain ("candidate strain" 54) corresponding to the minimum 52 is noted. The value of stress appearing on the stress-strain curve for data set 28 and corresponding to the candidate strain 54 is the "candidate residual seal force" 56. The preceding step is repeated for each of the second derivative analogues derived using each of the selected data smoothing spans, resulting in a candidate residual seal force 56 corresponding to each of the selected data smoothing spans for each data set 28.

Figure 7:
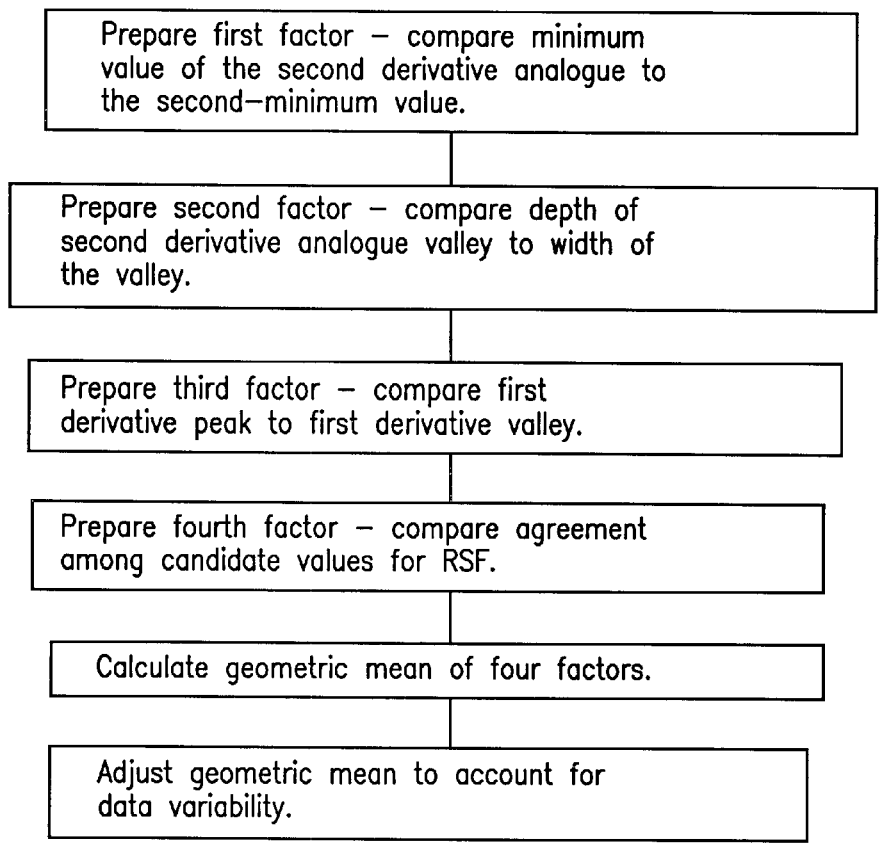
FIG. 7 is a detail flow chart of preparation of a confidence level.

From FIGS. 2 and 7, the algorithm next determines a confidence level for each of the candidate residual seal forces 56. The confidence level is a relative measure of the reliability of a candidate residual seal force 56 calculation. The confidence level is calculated by taking the geometric mean of four factors, followed by adjusting the result to account for data variability.

The first confidence factor (FIG. 7) is based on the relationship between the second derivative minimum 52 and the next lowest minimum 58 (FIG. 6). The next lowest minimum 58 may appear at any data point in data set 28 and represents an alternative value for residual seal force 56. In the ideal case there would be no next lowest minimum 58, but in real cases, particularly with small smoothing spans, there are sometimes other potential minima 58. The greater the difference in these minima 52, 58, the greater the confidence that the minimum 52 found represents the actual residual seal force. The factor is calculated as follows:

First factor=(lowest minimum−next lowest minimum)*33/next lowest minimum.

The calculation results in a factor of zero when there is no difference, and a factor of 100 when the lowest minimum is approximately four times the next lowest minimum.

Figure 8:
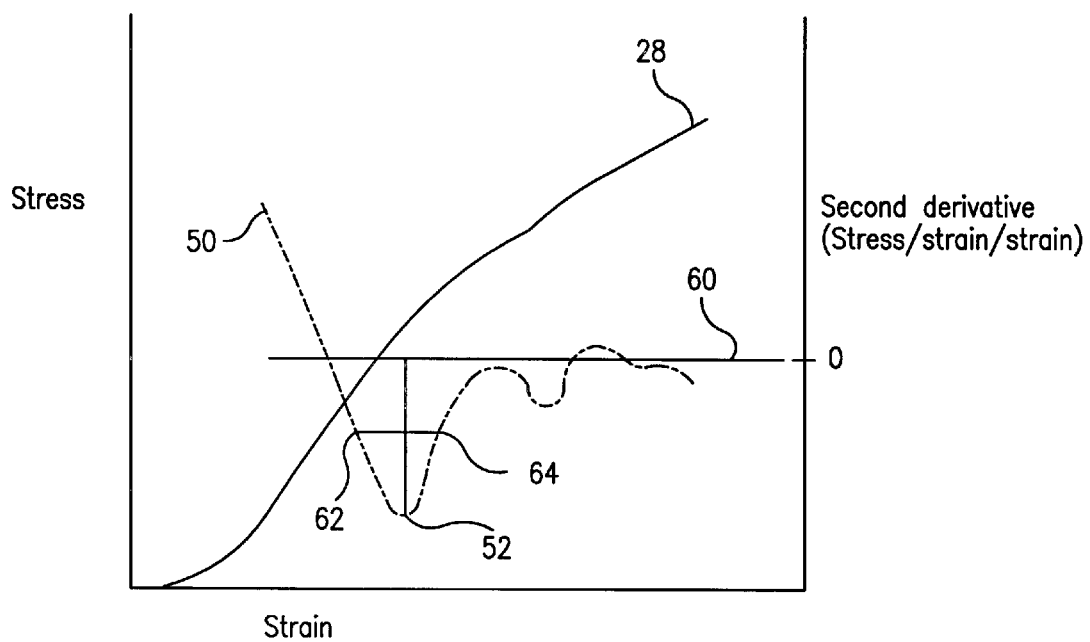
FIG. 8 is an example of derivation of the second confidence factor.

The second confidence factor (FIG. 7) is based on the relationship between the value of the second derivative minimum 52 and the width of the valley in which the minimum 52 resides. As shown by FIG. 8, the value of the second derivative analogue minimum 52 is the absolute value of the difference between that minimum 52 and zero. FIG. 8 shows an example zero line 60. The second derivative analogue minimum 52 defines a valley in the second derivative analogue curve. The width of the valley is the number of data points between the points 62, 64 where the second derivative analogue rises above ½ of the minimum 52. The narrower and deeper the valley, the sharper the definition of the knee, thus the more precisely its position is defined and the greater the confidence in the candidate residual seal force 56. The second factor is calculated as:

Second Factor=value of minimum/(width of valley/number of data points)/100

Where "Number of data points" is the total number of data points in a data set 28.

The third confidence factor is based on the total drop in the first derivative analogue from the first derivative analogue local maximum 46 (FIG. 5) to the first derivative analogue local minimum 48. The difference in first derivative analogue local maximum 46 and local minimum 48 is the total change in slope for the force curve across the "knee". The greater this change, the greater the confidence in the location of the "knee" and the greater the confidence in the candidate residual seal force 56. The third factor is calculated as:

Third Factor=(first derivative analogue local maximum−first derivative analogue local minimum)/first derivative analogue local maximum*200

The third factor calculation yields a factor of zero when the local maximum 46 and local minimum 48 are equal, and a factor of 100 when the local maximum 46 is twice the local minimum 48.

The fourth confidence factor is based on how many of the residual seal force candidates 56 are within 10% of the residual seal force candidate 56 in question. If a residual seal force candidate value 56 agrees with the values of other candidates, the value is entitled to greater confidence. The calculation is as follows:

Fourth factor=100*(number of residual seal force candidates within 10% of candidate in question)/total number of candidates The formulae for some of the confidence factors may yield a result greater than 100. If so, then the value of that factor is limited to 100. The four factors are geometrically averaged (the fourth root of the product), giving an initial confidence level from 0 to 100.

Initial confidence level=(factor one*factor two*factor three*factor four)$^{1/4}$ The last step in developing the confidence level (FIG. 7) is to adjust the initial confidence level to account for variability in the data. A hysteresis band 66 (FIG. 9) is added to the graph 50 of the second derivative analogue. The hysteresis band 66 extends ¼ of the value of the second derivative minimum 52 above and below the zero line 60 of the second derivative analogue graph 50. To account for data variability, the number of times that the second derivative analogue graph 50 crosses from one side of the hysteresis band 66 to the other side is counted. This is a measure of the smoothness or consistency of the stress-strain curve. The number of crossings is subtracted from the initial confidence level to arrive at a final confidence level, as follows:

Final confidence level=initial confidence level−number of crossings

Figure 9:
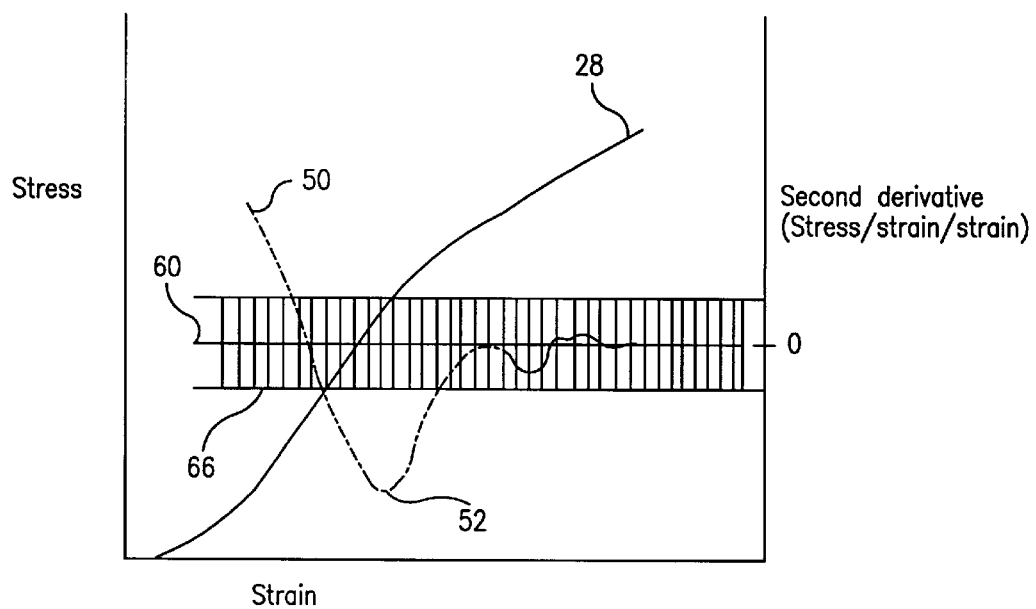
FIG. 9 is an example of a hysteresis band used to adjust the geometric mean of factors one through four.

In the example of FIG. 9, the graph of the second differential analogue 50 crosses the hysteresis band 66 one time. In the example of FIG. 9, the initial confidence level will be reduced by one.

A final confidence level is calculated for each candidate residual seal force 56. The candidate residual seal forces 56 are ranked by confidence level. The residual seal force candidate 56 corresponding to the data smoothing span resulting in the highest confidence level and meeting a preselected minimum confidence level is selected as the final residual seal force for that data set 28.

Once a residual seal force value for a data set 28 is determined, the data collection and analysis process is repeated. Three data sets 22 are collected and three values of final residual seal force are determined. To be accepted, the three residual seal force values must be within ±20% of one of the residual seal force values. If a group of data sets 28 do not yield valid residual seal force values or if the values are too far apart, additional data sets 28 are collected. Collection of additional data ends when three values of residual seal force are within ±20% of one of the residual seal force values or a predetermined maximum number of tries is reached.

When three residual seal force values are in sufficient agreement, the residual seal force values are arithmetically averaged and displayed to an operator. The push rod 24 of press 26 retreats from the container 4 and anvil 22 just enough to allow the container 4 and anvil 22 to be removed and replaced for the next test. All calculations and measurements are conducted automatically.

FIGS. 11A through 11F comprise a detailed flow chart of the operation of the apparatus and method of the invention. FIGS. 11A through 11F does not include error handling, off line operations and setup and configuration.

Any suitable press 26 may be used to implement the method of the present invention. The preferred apparatus is a specialized, purpose-built automated press 26 designed to meet the needs of pharmaceutical production. A block diagram of the preferred apparatus appears at FIG. 10. The preferred apparatus uses a programmable logic controller 68 ("PLC") to control the function of the press 26 (FIG. 1) and for all data collection, manipulation and display. The PLC 68 receives instructions entered by keypad on a user interface 70 by an operator. The PLC 68 communicates with motor controller 72, which in turn controls motor assembly 74. PLC 68 may instruct the motor controller to direct motor assembly 74 to move the push rod 24 (FIG. 1) toward the base 20 of the press 26. The base 20 of the press 26 incorporates a force transducer 76 communicating with the PLC 68. If the moving push rod 24 encounters an object (such as a container 4 to be tested), the force transducer 76 informs the PLC 68 of the force exerted by the container 4. A position encoder 78 simultaneously informs the PLC 68 of the position of push rod 24. The PLC 68 records the resulting data set 28 (FIG. 3) comprising stress data and strain data in random access memory, creating no permanent data record. The PLC 68 can be instructed to send data to a serial port 80, from which the data may be delivered to another device, such as a personal computer 82, for data storage or further manipulation. After completion of the testing for a container 4, the PLC 68 causes a final result for residual seal force to be exhibited to an operator on a display located on the user interface 70.

The PLC 68 of the preferred device controls the advance and retreat of the push rod 24 and conducts all calculations, including without limitation determination of the candidate residual seal forces 56 (FIG. 6) and determination of the confidence level (FIG. 7). The PLC 68 selects the candidate residual seal force 56 corresponding to the highest confidence level and determines whether additional data and additional calculation are required. A PLC 68 is preferred to a general-purpose computer such as a personal computer because the PLC 68 is a relatively simple device and is accepted as reliable and verifiable by the pharmaceutical industry and by the governmental bodies regulating the pharmaceutical industry.

The preferred apparatus is designed to accommodate the range of container 4 sizes used in the pharmaceutical industry and to be capable of applying forces appropriate to closures 2 of pharmaceutical containers 4. The housing of the preferred apparatus is composed primarily of stainless steel, the material preferred for process and testing equipment by pharmaceutical manufacturers. The preferred apparatus is equipped with safety features required by the pharmaceutical industry, such as an emergency stop switch and a guard to protect an operator from injury from the moving push rod of the press or from a broken container.

The following are specifications of one example of an actual apparatus implementing the method of the invention. Other specification sets are possible and can tailor the preferred apparatus to an application.

Example Specifications

Container 4 sizes accommodated include container 4 diameters from ½ inch to 3½ inches, and container 4 heights (including container 4, resilient member 12, and cap 14) from 1 inch to 7¼ inches. A wide variety of cap 14 styles and sizes can be accommodated with specific anvils 22. Cap 14 sizes including 8, 11, 13, 16.5, 20, 28, 30, and 32 mm are supported. Residual seal forces in the range of 5 lbf. to 60 lbf can be measured.

To test a container 4, an operator selects a range for the expected residual seal force (RSF), which determines the maximum force applied to the button 16 or cap 14. Example ranges are:

| Min. RSF | Max. RSF | Max Force |
|---|---|---|
| 5 | 15 | 30 |
| 10 | 20 | 40 |
| 15 | 25 | 50 |
| 20 | 40 | 70 |
| 30 | 60 | 90 |

Figure 10:
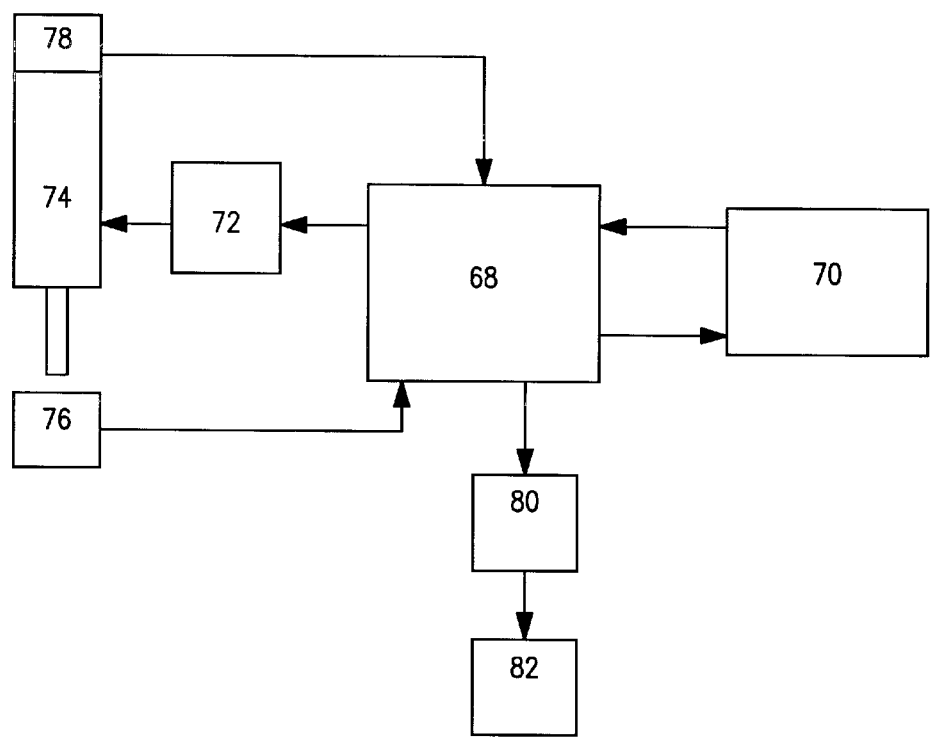
FIG. 10 is block diagram of the preferred apparatus.
Figure 11A:
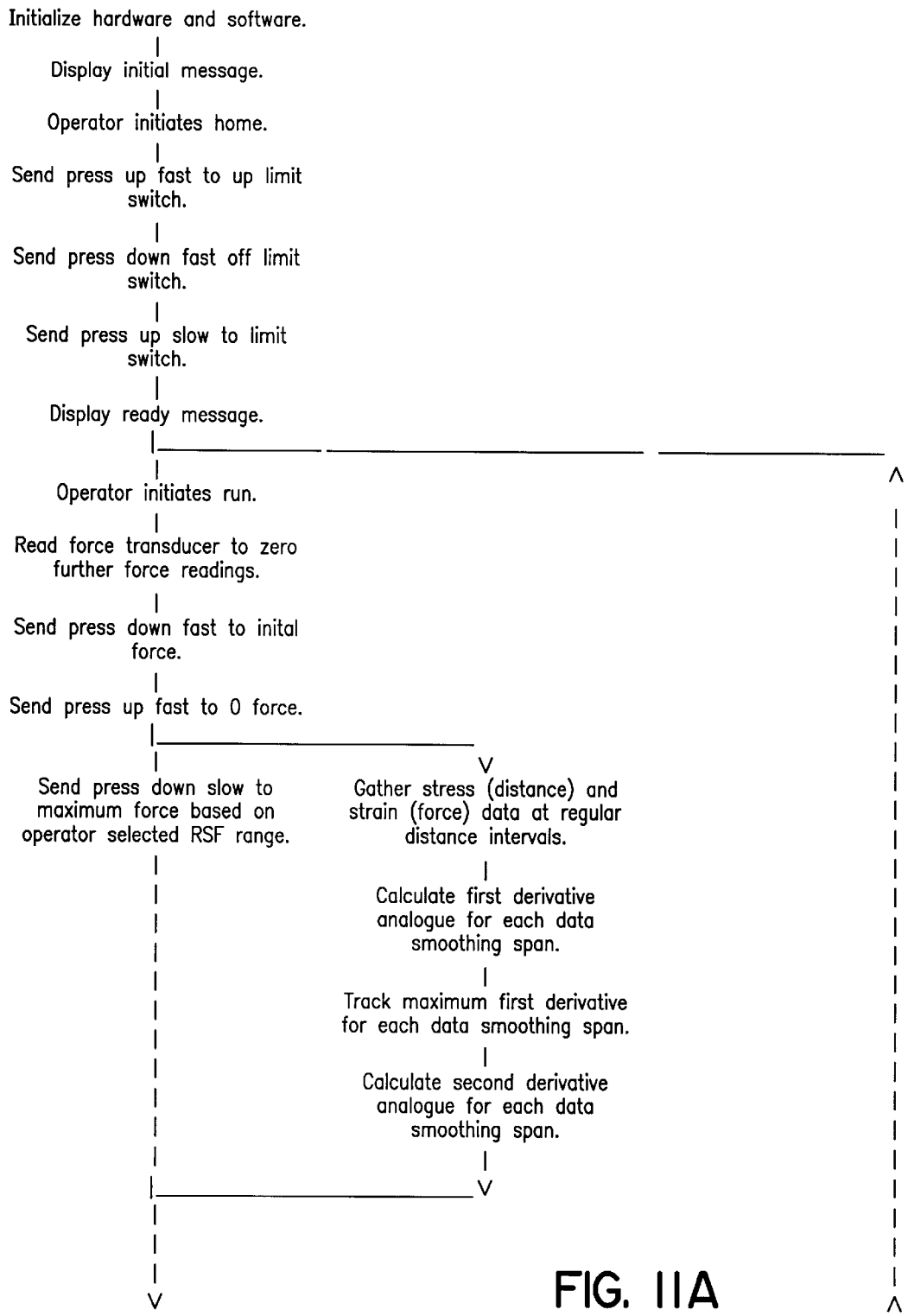
Figure 11B:
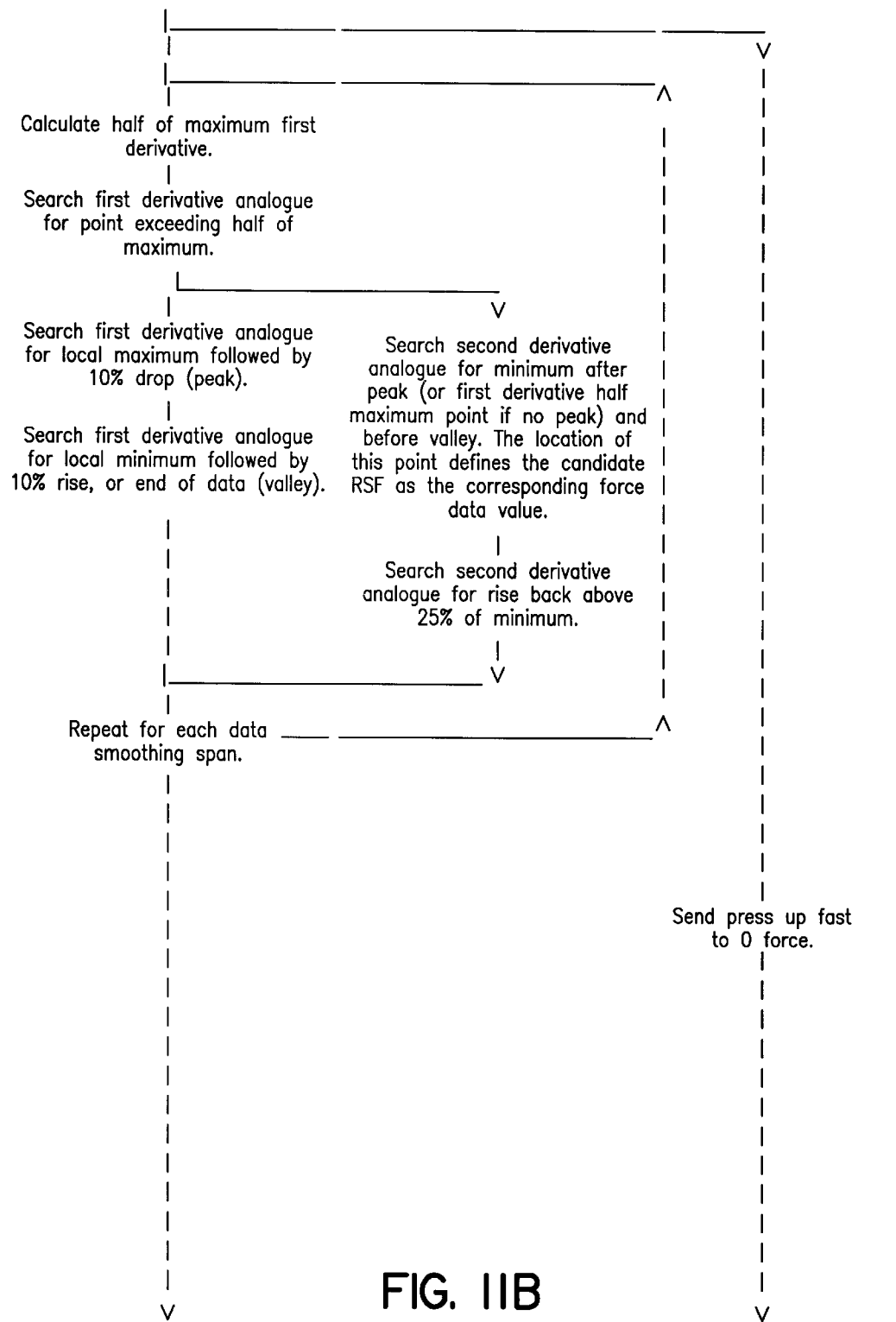
Figure 11C:
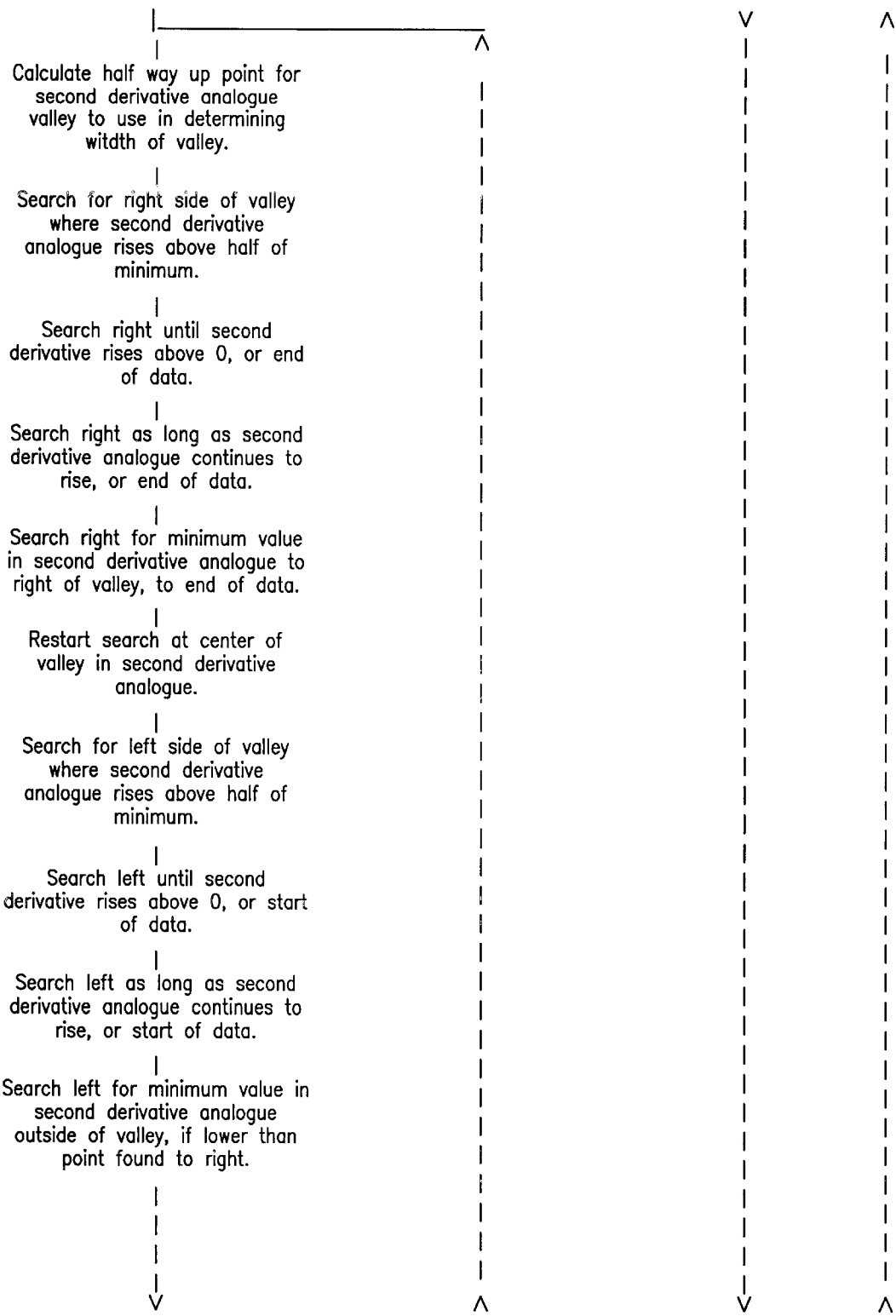
Figure 11E:
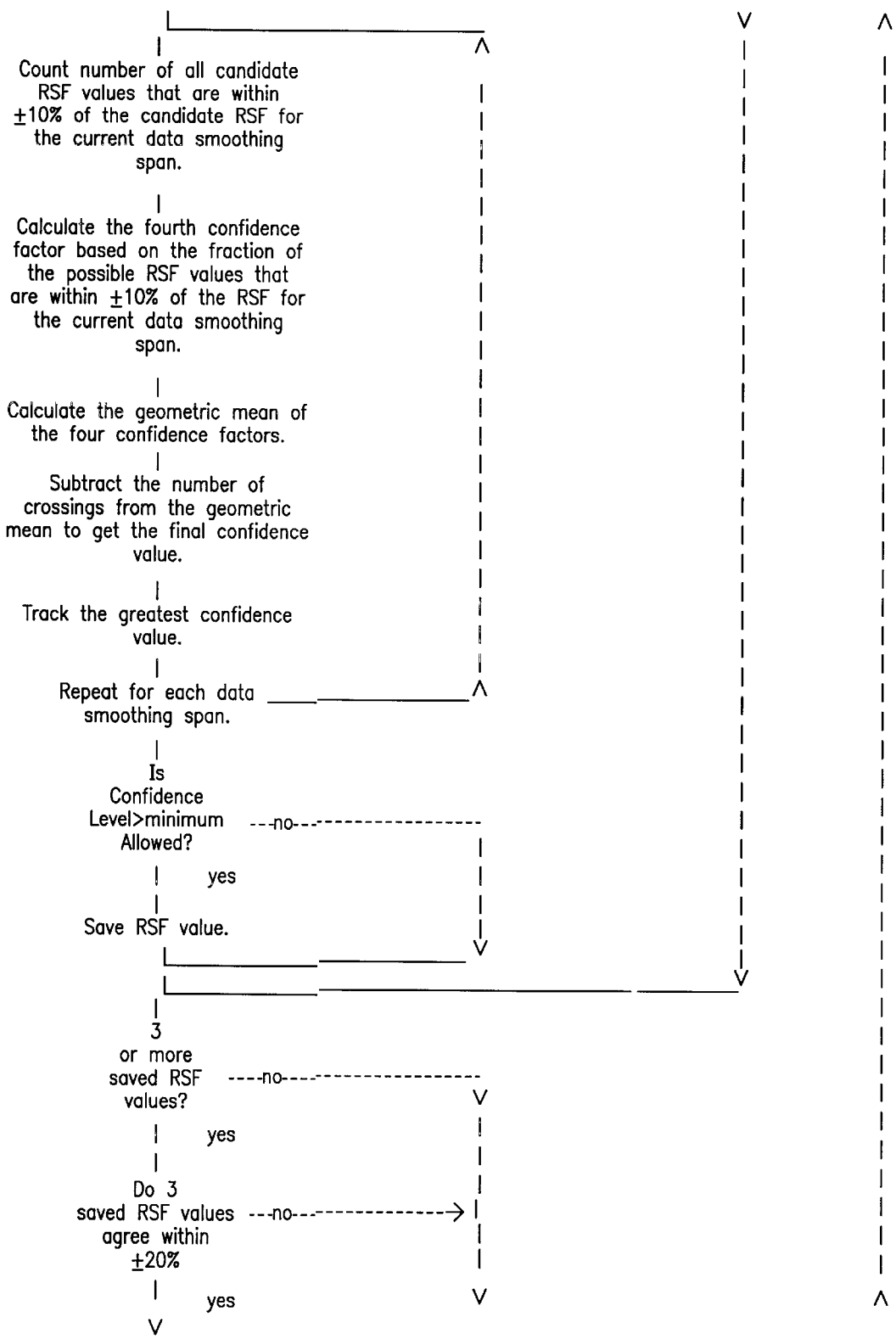
Figure 11F:
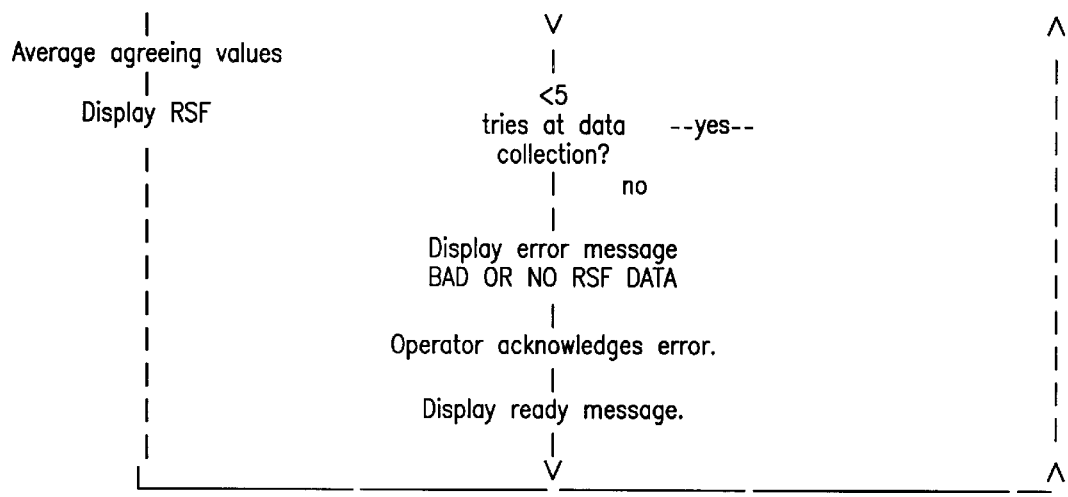

As illustrated by FIG. 1, the container 4 to be tested is placed on the base 20 in a container holder 18 that is specific to the container 4 diameter. The container holder 18 ensures the container 4 is centered over the force transducer 76 (FIG. 10). An anvil 22 specific to the cap 14 size and type is placed on the top of the button 16. The top of the anvil 22 is spherical to minimize any effects from the container 4 and the cap 14 being out-of-parallel. When the container 4 is ready for testing, the operator touches the run button. The data collection, analysis, and reporting process proceeds automatically under control of a PLC 68.

The press 26 is initialized, including setting the force reading to zero. The PLC 68 instructs the motor controller 72 to activate the motor assembly 74, advancing the push rod 24 toward the anvil 22, contacting the anvil 22 and applying an initial force to the closure 2. The push rod 24 then retreats, disengaging from the anvil 22 until the force drops to approximately zero. The push rod 24 then advances toward the anvil 22 at a slow speed of approximately 0.010 inches/sec. The PLC records the travel of the push rod 24 as communicated by the position indicator 78. The PLC also records the corresponding force measurements as communicated by the force transducer 76. Force readings are taken automatically every 0.001 inch or less of travel. The force is measured in units of 0.01 lbf. The push rod 24 automatically advances until the maximum force is reached, based on the RSF range set by the operator. Once the maximum force is reached, the push rod 24 retreats from the anvil 22 until the push rod 24 returns to its starting position.

Some calculations and data analyses are performed by the PLC 68 simultaneously with data collection. The remaining data analysis is performed after the maximum force has been reached and the push rod 24 returns to its starting position. The measured residual seal force (RSF) is displayed on a user interface 70 on the press 26, and is made available on a serial port 80 for automatically placing the data in a spread sheet on a computer 82.

Any errors detected in the process are reported through the user interface 70. The errors currently defined are:

SAFETY SCREEN NOT CLOSED

MOTOR NOT RUNNING

TIMEOUT-NO CONTAINER FOUND

TIMEOUT-UP AFTER COLLECTING DATA

TIMEOUT-COLLECTING DATA, MOTOR RUNNING TOO SLOWLY

TIMEOUT-UP TO 0 FORCE

EXCESSIVE FORCE

LIMIT SWITCH REACHED

NO OR BAD RESIDUAL SEAL FORCE DATA

INTERRUPT OVERRUN ERROR

OPERATOR CANCELED OPERATION

Several controls are available for calibration or research purposes but are not used in normal operation. One control triggers a mode in which the force is continuously displayed on the user interface 70. This allows calibration of the strain gauge amplifier and motor controller to be performed.

For research or validation purposes, a special mode will be available that provides both raw and some result data through the serial port 80. This will allow the raw force data to be dumped directly into a spreadsheet of a computer 82.

The instrument includes a safety enclosure to protect the operator in the unlikely event of glass breakage or slippage, and to keep fingers away from the moving press. A jog up/down control allows the operator to manually move the push rod 24 up or down. Other controls allow the operator to cancel any data read sequence. The jog down function is limited by a maximum allowable force to protect the apparatus and the vial. The residual seal force readings are completely objective and no operator subjectivity is involved in the measuring process.

Many different embodiments of the above invention are possible. This application is intended to address all possible embodiments and is limited only as described in the following claims.

I claim:

1. A method for determining the residual seal force of a sealed closure-container assembly comprising the steps of:
   a. Applying a plurality of strains to said sealed closure after sealing, said plurality of strains defining strain data;
   b. measuring a plurality of stresses exerted by said closure in response to each of said plurality of strains, said stresses defining stress data, said strain data and said stress data defining a data set;
   c. applying to said data set an algorithm designed to determine from the pattern of change in the relationships of stress verses strain data, the value which is representative of the stress reaching the residual seal force in the container closure assembly.

2. The method of claim 1, said algorithm utilizing a second derivative analogue minimum of said data set to determine said residual seal force.

3. The method of claim 2, said algorithm utilizing a second derivative.

4. The method of claim 3, comprising the additional steps of:
   a. determining a confidence level for each of said candidate residual seal forces; and
   b. determining a highest of said confidence levels;
   c. selecting said candidate residual seal force corresponding to said highest confidence level.

5. The method of claim 4, said determining of said confidence level comprising:
   a. determining a plurality of confidence factors;
   b. combining of said plurality of confidence factors.

6. The method of claim 5, said determining of said plurality of confidence level factors comprising determining a first factor, said first factor comparing said second derivative analogue minimum and a next-lowest minimum of said second derivative analogue.

7. The method of claim 5, said determining of said plurality of confidence factors comprising determining a second factor, said second factor comparing a value of said second derivative analogue minimum and a width of a second derivative analogue valley.

8. The method of claim 5, said determining of said plurality of confidence factors comprising determining a third factor, said third factor comparing a first derivative analogue local maximum and a first derivative analogue local minimum.

9. The method of claim 5, said determining of said plurality of confidence levels comprising determining a fourth factor, said fourth factor comparing each of said candidate seal forces to all other candidate seal forces derived for said data set.

10. The method of claim 5, said combining of said plurality of confidence factors comprising calculating a geometric mean of said confidence factors.

11. The method of claim 10 further comprising adjusting said geometric mean to consider data variability.

12. The method of claim 11, said adjusting said geometric mean comprising:
   a. preparing a hysteresis band for said second derivative analogue;
   b. adjusting said confidence level based upon said variability of said data about said hysteresis band.

13. The method of claim 12 comprising the additional step of utilizing said residual seal force to control a process.

14. The method of claim 5, said second derivative analogue minimum occurring within a strain range of interest.

15. The method of claim 14, said strain range of interest falling within strain values defined by a first derivative analogue local maximum and a first derivative analogue local minimum for said data set.

16. An apparatus for determining a residual seal force of a sealed closure-container assembly comprising:
   a. an automated press compressing said sealed closure after sealing;
   b. a programmable logic controller for controlling said press;
   c. a position encoder transmitting a plurality of strain data to said programmable logic controller;
   d. a stress transducer transmitting a plurality of stress data to said programmable logic controller, said strain data and said stress data defining a data set;
   e. applying to said data set an algorithm designed to determine from the pattern of change and the relationships of stress verses strain data, the value which is representative of the stress reaching the residual seal force.

17. The apparatus of claim 16, said programmable logic controller being programmed to utilize a second derivative analogue minimum of said data set to determine said residual seal force.

18. The apparatus of claim 17, said programmable logic controller being programmed to determine said second derivative analogue minimum for each of a plurality of data smoothing spans to define a plurality of candidate residual seal forces.

19. The apparatus of claim 18, said programmable logic controller being programmed to:
   a. determine a confidence level for each of said candidate residual seal forces; and
   b. determine a highest of said confidence levels;
   c. select said candidate residual seal force corresponding to said highest confidence level.

20. The apparatus of claim 19, said programmable logic controller being programmed to determine said confidence level by:
   a. determining a plurality of confidence factors;
   b. combining of said plurality of confidence factors.

21. The apparatus of claim 20, said programmable logic controller being programmed to determine a first confidence factor, said first confidence factor comparing said second derivative analogue minimum and a next-lowest minimum of said second derivative analogue.

22. The apparatus of claim 20, said programmable logic controller being programmed to determine a second factor, said second factor comparing a value of said second derivative analogue minimum and a width of a second derivative analogue valley.

23. The apparatus of claim 20, said programmable logic controller being programmed to determine a third factor, said third factor comparing a first derivative analogue local maximum and a first derivative analogue local minimum.

24. The apparatus of claim 20, said programmable logic controller being programmed to determine a fourth factor, said fourth factor comparing each of said candidate seal forces to all other candidate seal forces derived for said data set.

25. The apparatus of claim 20, said programmable logic controller being programmed to combine said confidence factors by calculating a geometric mean of said confidence factors.

26. The apparatus of claim 25, said programmable logic controller being programmed to adjust said geometric mean to consider data variability.

27. The apparatus of claim 26, said programmable logic controller being programmed to adjust said geometric mean to consider data variability by:
   a. preparing a hysteresis band for said second derivative analogue;
   b. adjusting said confidence level based upon said variability of said data about said hysteresis band.

28. The apparatus of claim 17, said programmable logic controller being programmed to determine said second derivative analogue minimum within a strain range of interest.

29. The apparatus of claim 28, said programmable logic controller being programmed to determine said strain range of interest within strain values defined by a first derivative analogue local maximum and a first derivative analogue local minimum for said data set.

30. A method for evaluating the residual said force of a closure of a container comprising the steps of:
   a. applying a plurality of strains to said closure, said plurality of strains defining strain and data;
   b. measuring a plurality of stresses exerted by said closure in response to each of said plurality of strains, said stresses defining stress data, said strain data and said stress data defining a data set;
   c. applying an algorithm to said data set, said algorithm defining a residual seal force;
   d. said algorithm utilizing a second derivative analogue minimum of said data set to determine said residual seal force.

31. An apparatus for evaluating a residual seal force of a closure of a container comprising:
   a. an automated press compressing said closure;
   b. a programmable logic controller controlling said press;
   c. a position encoder transmitting a plurality of strain data to said programmable logic controller;
   d. said programmable logic controller being programmed to apply an algorithm to said data set to determine residual seal force;
   e. said programmable logic controller being programmed to utilize a second derivative analogue minimum of said data set to determine said residual seal force;
   f. said programmable logic controller being programmed to utilize a second derivative analogue minimum of said data set to determine said residual seal force.

* * * * *